(12) United States Patent
Miyazaki

(10) Patent No.: US 8,577,442 B2
(45) Date of Patent: Nov. 5, 2013

(54) MAGNETIC RESONANCE IMAGING APPARATUS AND MAGNETIC RESONANCE IMAGING METHOD

(75) Inventor: Mitsue Miyazaki, Mount Prospect, IL (US)

(73) Assignees: Kabushiki Kaisha Toshiba, Minato-Ku, Tokyo (JP); Toshiba Medical Systems Corporation, Otawara-Shi, Tochigi-Ken (JP)

( * ) Notice: Subject to any disclaimer, the term of this patent is extended or adjusted under 35 U.S.C. 154(b) by 362 days.

(21) Appl. No.: 12/699,169

(22) Filed: Feb. 3, 2010

(65) Prior Publication Data
US 2010/0249574 A1 Sep. 30, 2010

(30) Foreign Application Priority Data

Mar. 24, 2009 (JP) .................................. 2009-072369
Jul. 2, 2009 (JP) .................................. 2009-158188

(51) Int. Cl.
*A61B 5/055* (2006.01)
(52) U.S. Cl.
USPC ............ 600/413; 600/500; 600/519; 600/521
(58) Field of Classification Search
USPC ......... 600/410, 413, 428, 500, 508, 509, 519, 600/521
See application file for complete search history.

(56) References Cited

U.S. PATENT DOCUMENTS

| 6,801,800 B2 * | 10/2004 | Miyazaki et al. | 600/410 |
| 7,020,511 B2 * | 3/2006 | Boyd et al. | 600/428 |
| 7,164,268 B2 * | 1/2007 | Mugler et al. | 324/307 |
| 7,256,578 B2 * | 8/2007 | Oshio | 324/306 |

FOREIGN PATENT DOCUMENTS

| JP | 2002-143125 | 5/2002 |
| JP | 2004-329614 | 11/2004 |
| JP | 2005-305151 | 11/2005 |
| JP | 2007-000630 | 1/2007 |
| JP | 2008-125986 | 6/2008 |
| JP | 2009-056313 | 3/2009 |

* cited by examiner

*Primary Examiner* — Ruth S Smith
(74) *Attorney, Agent, or Firm* — Nixon & Vanderhye PC (57) ABSTRACT

A magnetic resonance imaging apparatus includes a data acquisition unit and an image generating unit. The data acquisition unit sets a delay time from a reference wave based on heart rate information or peripheral pulse wave information previously acquired from an object and acquires MR signals by an imaging scan with a delay time and in synchronization with a blood flow beat. The delay time represents a time phase for image data acquisition timing in synchronization with the beat. The image generating unit generates a blood flow image based on the magnetic resonance signals.

21 Claims, 7 Drawing Sheets

TI=150ms; TEeff=80ms

| HR | <50 | | 50-60 | | 60-70 | | 70-80 | | 80-90 | | >90 | |
|---|---|---|---|---|---|---|---|---|---|---|---|---|
| REGION | SYS | DIAS | SYS | DIAS | SYS | DIAS | SYS | DIAS | SYS | DIAS | SYS | DIAS |
| ILIAC | 90 | 650 | 100 | 620 | 110 | 580 | 110 | 560 | 90 | 520 | 90 | 480 |
| THIGH | 100 | 670 | 110 | 630 | 120 | 590 | 120 | 570 | 100 | 530 | 100 | 490 |
| CALF | 110 | 670 | 120 | 650 | 120 | 600 | 120 | 580 | 100 | 540 | 100 | 490 |
| HAND | 90 | 650 | 100 | 630 | 110 | 590 | 110 | 570 | 100 | 530 | 90 | 480 |
| FOOT | 110 | 680 | 120 | 640 | 120 | 600 | 120 | 580 | 110 | 530 | 100 | 490 |
| 70%STENOSIS | +40 | +40 | +40 | +40 | +40 | +40 | +40 | +40 | +40 | +40 | +40 | +40 |

UNIT ms

MAGNETIC RESONANCE IMAGING APPARATUS AND MAGNETIC RESONANCE IMAGING METHOD

BACKGROUND

1. Technical Field

The present disclosure relates to a MRI (magnetic resonance imaging) apparatus and a magnetic resonance imaging method which magnetically excites nuclear spins of an object with an RF (radio frequency) signal having the Larmor frequency and reconstructs an image based on NMR (nuclear magnetic resonance) signals generated due to the excitation, and more particularly, to a magnetic resonance imaging apparatus and a magnetic resonance imaging method which make it possible to perform MRA (Magnetic Resonance Angiography) in which a blood flow image is acquired.

2. Related Art

Magnetic Resonance Imaging is an imaging method which magnetically excites nuclear spins of an object set in a static magnetic field with an RF signal having the Larmor frequency and reconstructs an image based on NMR signals generated due to the excitation.

In the field of MRI, MRA is known as a method for obtaining an image of a blood flow. MRI without using a contrast medium is referred to as non-contrast MRA. As non-contrast enhanced MRA, an FBI (fresh blood imaging) method synchronized with an ECG (electro cardiogram) signal captures a pumping blood flow ejected from the heart, thereby satisfactorily representing a blood vessel (for example, refer to Japanese Publication of Patent Application No. 11-239571).

As related technology used with the FBI method, an ECG-prep procedure measures an appropriate delay time for synchronization with an ECG signal. The ECG-prep scan is a preparation scan used to decide upon an appropriate delay time for synchronization with an ECG signal and is performed prior to an FBI scan for imaging. The FBI scan is subsequently performed using the ECG delay time decided upon by the ECG-prep scan. The ECG-prep scan obtains plural single-shot images at mutually different time phases by acquiring data at gradually changed delay times from an R wave of an ECG signal. By selecting an ECG-prep scan image in which blood vessels are appropriately depicted from among the plural ECG-prep scan images, the ECG delay time for the FBI scan can be determined. This allows a high velocity blood flow to be depicted at a time phase corresponding to a lower flow velocity.

As a technology for selecting the most appropriate ECG-prep image from the plural ECG-prep images acquired by the ECG-prep scan, FBI-NAVI is also devised (for example, refer to Japanese Publication of Patent Application No. 2008-23317).

However, there is a problem in that it is conventionally difficult to determine the delay time for ECG synchronization, i.e., a time phase as an imaging timing without reference to ECG-prep images by a skilled operator.

BRIEF SUMMARY

The present exemplary embodiment has been made in light of the conventional situations, and it is an object of the present exemplary embodiment to provide a magnetic resonance imaging apparatus and a magnetic resonance imaging method which make it possible to determine an appropriate time phase to acquire data for a blood flow image more easily without requiring a special knowledge and technique.

The present exemplary embodiment provides a magnetic resonance imaging apparatus comprising: a data acquisition unit configured to set a delay time from a reference wave based on heart rate information or peripheral pulse wave information previously acquired from an object and acquire magnetic resonance signals by an imaging scan with the set delay time synchronized with a beat, the delay time representing a time phase of a data acquisition timing synchronized with the beat, and an image generating unit configured to generate a blood flow image based on the magnetic resonance signals.

The present exemplary embodiment also provides a magnetic resonance imaging apparatus comprising: a storage unit configured to store plural delay times from a reference wave for imaging synchronized with a beat, the plural delay times being related with pieces of heart rate information or peripheral pulse wave information and each representing a time phase at a data acquisition timing; a data acquisition unit configured to acquire a delay time corresponding to heart rate information or peripheral pulse wave information previously acquired from an object to be imaged, set the acquired delay time as an imaging condition and acquire magnetic resonance signals by an imaging scan with the set delay time synchronized with a beat, the delay time being acquired from said storage unit; and an image generating unit configured to generate a blood flow image based on the magnetic resonance signals.

The present exemplary embodiment also provides a magnetic resonance imaging method comprising: setting a delay time from a reference wave based on heart rate information or peripheral pulse wave information previously acquired from an object and acquiring magnetic resonance signals by an imaging scan with the set delay time synchronized with a beat, the delay time representing a time phase of a data acquisition timing in imaging synchronized with the beat, and generating a blood flow image based on the magnetic resonance signals.

The present exemplary embodiment also provides a magnetic resonance imaging method comprising: storing plural delay times from a reference wave in imaging synchronized with a beat, the plural delay times being related with pieces of heart rate information or peripheral pulse wave information and each representing a time phase at a data acquisition timing; acquiring a delay time corresponding to heart rate information or peripheral pulse wave information previously acquired from an object to be imaged, setting the acquired delay time as an imaging condition and acquiring magnetic resonance signals by an imaging scan with the set delay time synchronized with a beat, the delay time being acquired from the stored plural delay times; and generating a blood flow image based on the magnetic resonance signals.

The magnetic resonance imaging apparatus and the magnetic resonance imaging method as described above make it possible to acquire data for a blood flow image more easily without requiring a special knowledge and technique.

DESCRIPTION OF THE PREFERRED EMBODIMENTS

A magnetic resonance imaging apparatus and a magnetic resonance imaging method according to embodiments of the present invention will be described with reference to the accompanying drawings.

(Configuration and Function)

Figure 1:
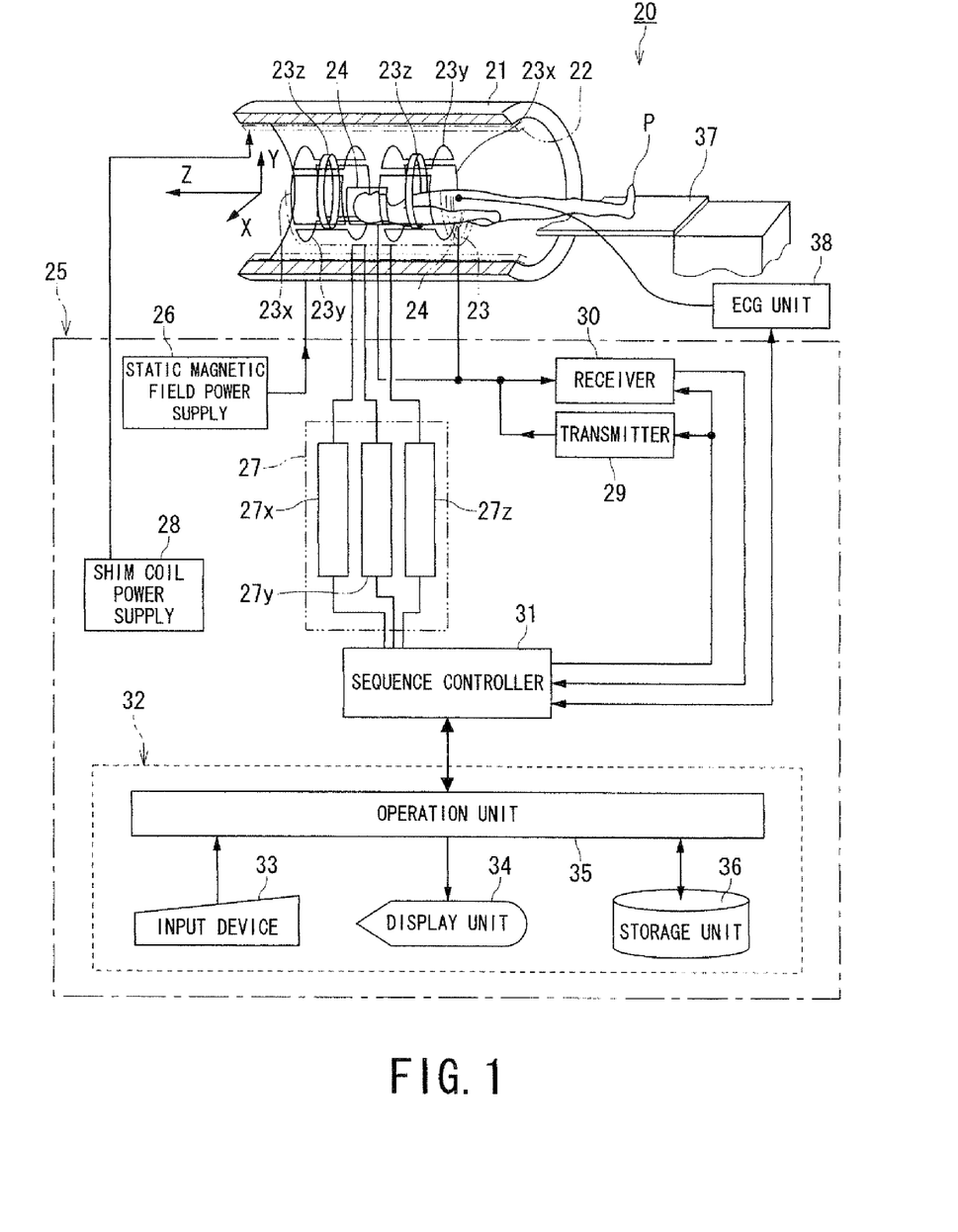
FIG. 1 is a block diagram showing a magnetic resonance imaging apparatus according to an embodiment of the present invention.

FIG. 1 is a block diagram showing a magnetic resonance imaging apparatus according to an embodiment of the present invention.

A magnetic resonance imaging apparatus 20 includes a static field magnet 21 for generating a static magnetic field, a shim coil 22 arranged inside the static field magnet 21 which is cylinder-shaped, a gradient coil 23 and RE coils 24.

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input device 33, a display unit 34, a operation unit 35 and a storage unit 36.

The static field magnet 21 communicates with the static magnetic field power supply 26. The static magnetic field power supply 26 supplies electric current to the static field magnet 21 to get the function to generate a static magnetic field in a imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil 23 includes an X-axis gradient coil 23x, a Y-axis gradient coil 23y and a Z-axis gradient coil 23z. Each of the X-axis gradient coil 23x, the Y-axis gradient coil 23y and the Z-axis gradient coil 23z which is cylinder-shaped is arranged inside the static field magnet 21. The gradient coil 23 has also a bed 37 in the area formed inside it which is an imaging area. The bed 37 supports an object P. The RE coils 24 include a whole body coil (WBC: whole body coil), which is built in the gantry, for transmission and reception of RE signals and local coils, which are arranged around the bed 37 or the object P, for reception of RF signals.

The gradient coil 23 communicates with the gradient power supply 27. The X-axis gradient coil 23x, the Y-axis gradient coil 23y and the Z-axis gradient coil 23z of the gradient coil 23 communicate with the X-axis gradient power supply 27x, the Y-axis gradient power supply 27y and the Z-axis gradient power supply 27z of the gradient power supply 27 respectively.

The X-axis gradient power supply 27x, the Y-axis gradient power supply 27y and the Z-axis gradient power supply 27z supply currents to the X-axis gradient coil 23x, the Y-axis gradient coil 23y and the Z-axis gradient coil 23z respectively so as to generate gradient magnetic fields Gx, Gy and Gz in the X, Y and Z directions in the imaging area.

The RF coils 24 communicate with the transmitter 29 and/or the receiver 30. The transmission RF coil 24 has a function to transmit a RF signal given from the transmitter 29 to the object P. The reception RF coil 24 has a function to receive a MR signal generated due to an nuclear spin inside the object P which is excited by the RF signal to give to the receiver 30.

The sequence controller 31 of the control system 25 communicates with the gradient power supply 27, the transmitter 29 and the receiver 30. The sequence controller 31 has a function to store sequence information describing control information needed in order to make the gradient power supply 27, the transmitter 29 and the receiver 30 drive and generate gradient magnetic fields Gx, Gy and Gz in the X, Y and Z directions and an RF signal by driving the gradient power supply 27, the transmitter 29 and the receiver 30 according to a predetermined sequence stored. The control information above-described includes motion control information, such as intensity, impression period and impression timing of the pulse electric current which should be impressed to the gradient power supply 27.

The sequence controller 31 is also configured to give raw data to the computer 32. The raw data is complex data obtained through the detection of a NMR signal and A/D conversion to the NMR signal detected in the receiver 30.

The transmitter 29 has a function to give a RF signal to the RE coil 24 in accordance with control information provided from the sequence controller 31. The receiver 30 has a function to generate raw data which is digitized complex number data by detecting a MR signal given from the RE coil 24 and performing predetermined signal processing and A/D converting to the MR signal detected. The receiver 30 also has a function to give the generated raw data to the sequence controller 31.

In addition, an ECG unit 38 for acquiring an ECG (electro cardiogram) signal of the object P is provided with the magnetic resonance imaging apparatus 20. The ECG signal detected by the ECG unit 38 is outputted to the computer 32 through the sequence controller 31.

Note that, a PPG (peripheral pulse gating) signal representing a beat as pulse wave information may be acquired instead of an ECG signal representing a beat as heart rate information. A PPG signal is acquired by detecting a pulse wave of e.g. tip of a finger as an optical signal. When a PPG signal is acquired, a PPG signal detection unit is provided with the magnetic resonance imaging apparatus 20. Hereinafter, a case of acquiring an ECG signal will be described.

The computer 32 gets various functions by the operation unit 35 executing some programs stored in the storage unit 36 of the computer 32. Alternatively, some specific circuits having various functions may be provided with the magnetic resonance imaging apparatus 20 instead of using some of the programs.

Figure 2:
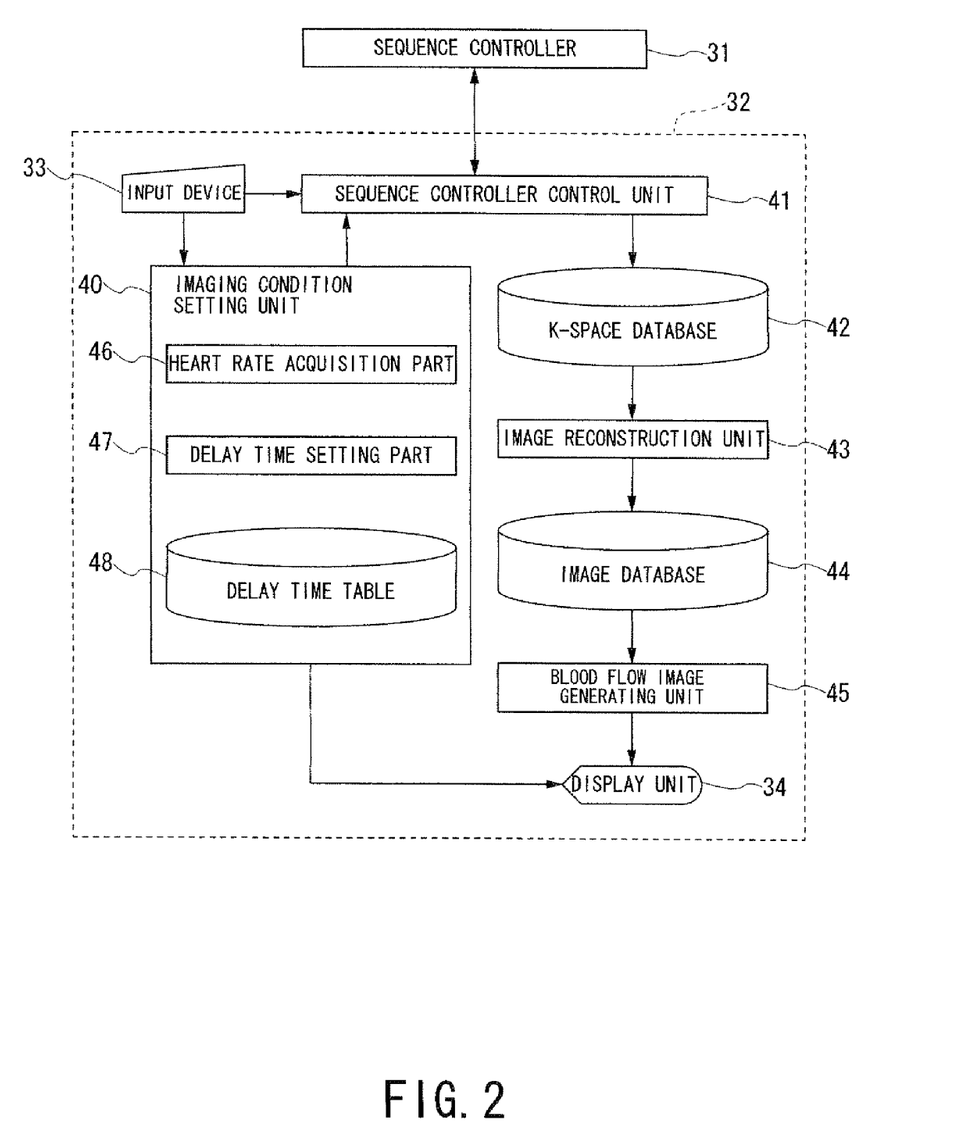
FIG. 2 is a functional block diagram of the computer 32 shown in FIG. 1.

FIG. 2 is a functional block diagram of the computer 32 shown in FIG. 1.

The computer 32 functions as an imaging condition setting unit 40, a sequence controller control unit 41, a k-space database 42, an image reconstruction unit 43, an image database 44 and a blood flow image generating unit 45. The imaging condition setting unit 40 includes a heart rate acquisition part 46, a delay time setting part 47 and a delay time table 48.

The imaging condition setting unit 40 has a function to set an imaging condition including a pulse sequence based on instruction from the input device 33 and to provide the set imaging condition to the sequence controller control unit 41. Especially, the imaging condition setting unit 40 has a function to set a pulse sequence to acquire a blood flow image synchronized with a heart rate such as an ECG signal or a PPG signal using heart rate information.

The methods of acquiring a blood flow image include a non-contrast-enhanced MRA method that does not use contrast medium and a contrast-enhanced MRA method that uses contrast medium. The non-contrast-enhanced MRA methods include FBI method, TOE (time of flight) method, steady state free precession (SSFP) method that produces a steady state of spins and FLOW PREP method. Therefore, a pulse sequence according to an arbitrary method out of the MRA methods described above can be set as an imaging condition.

FBI is a non-contrast-enhanced MRA method which acquires echo data repeatedly every plural heart rates with successive delays by a predetermined delay time from a trigger signal synchronized with a reference wave, such as an R wave, representing a cardiac time phase of an object P using a SE series of sequences such as a SSFP sequence and a FASE (fast asymmetric spin echo or fast advanced spin echo) sequence that uses a half Fourier method. According to the FBI method, a transverse relaxation (T2) component of magnetization in blood is recovered by passing plural heart rates and a water (blood) weighted image in which the T2 magnetization component of blood is enhanced) and can be obtained as a blood vessel image. In the FBI method, a three dimensional scan for acquiring echo data (volume data) for predetermined slice encode amounts is performed.

The TOF method is a method of acquiring a blood vessel image using an inflow effect of blood into an image section. That is, the TOF method is a method for imaging blood signals flowing into an image section subsequent to applying a saturation pulse. In the TOF method, a scan is performed at an earlier data acquisition timing using a FE (field echo) series of sequences and a longitudinal relaxation (T1) weighted image is acquired as a blood vessel image.

The Flow Prep method is a method for depicting arteries selectively by applying an RF pulse according to a maximum blood flow velocity of blood flowing in a targeted blood vessel to label the blood flow and imaging in a myocardial diastole phase.

The heart rate acquisition part 46 in the imaging condition setting unit 40 has a function to acquire heart rate information of an object P from the ECG unit 38 or a PPG unit not shown in the figure and provide a heart rate (HR) of the object P to the delay time setting part 47. The heart rate information includes a HR itself and a period between reference waves adjacent on an ECG signal or a PPG signal as well as an ECG signal or a PPG signal. When the ECG unit 38 or the PPG unit has function to calculate a HR, the heart rate acquisition part 46 is configured to acquire a HR from the ECG unit 38 or the PPG unit directly. The heart rate acquisition part 46 may be also configured to acquire an ECG signal, a PPG signal or a period between adjacent reference waves on an ECG or PPG signal from the ECG unit 38 or the PPG unit and calculate a HR based on the ECG signal or the PPG signal. For example, a HR can be calculated from a R-R between R waves on an ECG signal by equation (1).

$$R\text{-}R = 60000 \text{ ms}/HR \quad (1)$$

Note that, the heart rate acquisition part 46 may be also configured to calculate or acquire plural HRs and provide an average value of the plural HRs to the delay time setting part 47 for accuracy improvement. For example, the heart rate acquisition part 46 may acquire a HR around ten times and make the average value of the 10 HRs be the HR provided to the delay time setting part 47. It is thought that it only has to acquire a HR four to twenty times to calculate an average value for obtaining a HR with practical accuracy.

The delay time setting part 47 has a function to set an appropriate delay time from a reference wave as an imaging condition in a heart rate synchronous imaging method based on the HR acquired from the heart rate acquisition part 46. The setting methods of a delay time include a method of calculating a delay time from a KR using a calculating formula representing a relation between HRs and delay times and a method of preparing a table showing a relationship between HRs and delay times to acquire a delay time corresponding to an HR of an object P in reference to the table.

For example, it is reported that equation (2) is established approximately between a systole SD and a HR when a myocardial systole is denoted by SD. Note that, exactly, the numerical value 550 in equation (2) may be a different value for individual difference by gender and age. Therefore, the relation between a systole SD and a HR may be expressed by a quadratic expression or a high order more than second order expression.

$$SD = 550 - 2HR \quad (2)$$

Therefore, when data acquisition timing is desired to be set in a diastole, a systole SD can be estimated based on equation (2) and a delay time can be set so that the data acquisition timing becomes in a diastole. As a specific example, since R-R=1000 and SD=430 based on equation (1) and equation (2) when an HR is 60, it only has to set a delay time in as period of 570 ms after at least 430 ms from an R wave. That is, equation (3) that shows a relation between a delay time DT and an HR can be determined using a function f so that equation (2) is true.

$$DT = f(HR) \quad (3)$$

However, in the case of irregular heartbeat, an R-R interval may become extremely short and an HR may become large. In this case, a systole SD may become over-extended for following the heart rate when the systole SD is calculated by using a large HR as it is. That is, there is a possibility that a data acquisition timing becomes just before an R wave. Accordingly, the delay time setting part 47 has a function to correct a delay time DT calculated by equation (3) so that an appropriate delay time DT is set as an imaging condition even if an R-R interval becomes disordered. A delay time DT can be also corrected by multiplying by a coefficient determined empirically in advance. Note that, empirically, it is thought that a corrected delay time DTcor can be calculated as a practical value so long as a correction coefficient k is added to a delay time DT as shown in equation (4). The correction coefficient k can be acquired empirically in advance as described below.

$$DTcor = DT + k = f(HR) + k \quad (4)$$

Similarly, a relational expression between a HR and a diastole may be acquired in advance with an arbitrary method such as a test and a diastole may be estimated based on the relational expression between a HR and a diastole. A calculation expression showing a relation between a delay time DT and a HR can be also determined so that a delay time of data acquisition timing from a reference wave is set in a systole.

By the way, an imaging region of a blood flow image can be also set arbitrarily. Therefore, an imaging condition for blood flow imaging of a lower limb or coronary artery imaging can be set. However, a blood flow velocity is different depending on an imaging part. Therefore, an appropriate delay time from a reference wave of data acquisition timing may be also desired to be set with a higher accuracy as a value different depending on an imaging part. For that reason, a calculation expression showing a relation between a HR and a delay time can be also set for every imaging part. For example, since a blood flow velocity at a low end portion such as a lower limb is slower compared to that in a vicinity of heart, a delay time for a low end portion can be set longer than a delay time for a vicinity of heart. In this case, a delay time can be also determined depending on not only a distance from the heart to an imaging location but also a time difference between an ECG signal and a PPG signal acquired from a distal portion such as a finger of hand, and/or a difference in average blood flow velocities.

Additionally, there is a ratio of blood pressures in an ankle and a brachium (ABI: ankle brachial index) as an index showing a blood flow velocity. Accordingly, a calculation expression representing a relation between a HR and a delay time can be also set for every ABI value. Further, a blood flow velocity changes depending on extent of an affected area such as angiostenosis. Therefore, a calculation expression showing a relation between a HR and a delay time may be also determined for every index value indicating advancing extent of an affected area.

That is, a delay time can be corrected by determining a correction coefficient of delay time every imaging region, ABI value and/or index value showing advancing extent of an affected area together with a calculation expression representing a relation between a HR and a delay time and adding or multiplying a delay time calculated based on the calculation expression representing a relation between a HR and a delay time to or by a correction coefficient for every imaging region, ABI value and/or index value showing advancing extent of an affected area.

When a delay time is determined by a setting method of an imaging condition that sets a period from a reference wave, such as an R wave, representing a cardiac time phase to an application time of the first RF pulse or a gradient magnetic field pulse as a delay time, it may be preferable that the delay time is changed depending on a pulse sequence. For example, it may be preferable to set a delay time so that not an start timing of a sequence but the acquisition timing of data near the center of k-space becomes a desired timing in a diastole or a systole. Additionally, in the case of imaging under a fat saturation method such as a STIR (short TI inversion recovery) method and/or a CHESS (chemical shift selective) method, it is necessary to consider a delay time from a fat saturation pulse such as a STIR pulse and a CHESS pulse to a 90-degree excitation pulse. For example, in the case of imaging under a STIR method, it is necessary to consider an inversion time (TI) from a 180-degree IR pre-pulse to a 90-degree excitation pulse.

For that reason, the delay time setting part 47 has a function to correct the delay time DTcor corrected once to evade an influence of fluctuation in R-R based on a delay time DTF, such as a TI, of a fat saturation pulse and/or an effective echo time (effective TE). That is, the delay time setting part 47 can be configured to set a delay time DTcor by equation (5) wherein an imaging location, an effective TE and an index value showing advancing extent of an affected area is denoted by LOCATION, TEeff and INDEX respectively, for functions mentioned above. The TEeff becomes a different value depending on a data acquisition method such as centric data acquisition and sequential data acquisition. The parameters necessary for determination of a delay time can be input to the delay time setting part 47 from the input device 33.

$$DTcor=f(HR, \text{LOCATION}, \text{ABI}, \text{DTF}, \text{TEeff}, \text{INDEX})+k \quad (5)$$

Note that, when a delay time is set by a setting method of an imaging condition that sets the period from a reference wave, such as an R wave, showing a cardiac time phase to an acquisition timing of data near the center of k-space as a delay time directly, it is not necessary to consider a delay time, such as a TI, of a fat saturation pulse and a TEeff.

Figure 3:
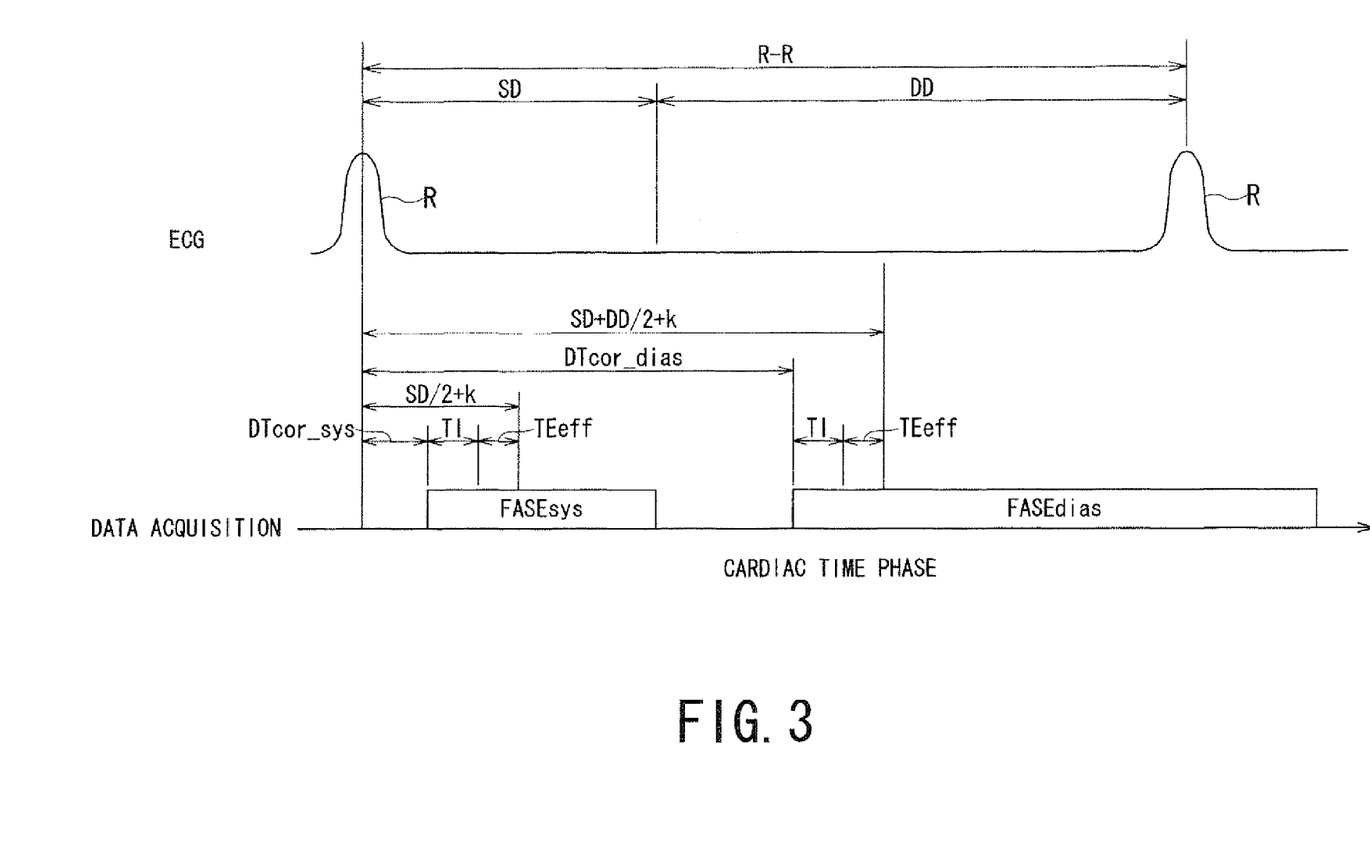
FIG. 3 is a chart explaining a method for determining a delay time in the delay time setting part shown in FIG. 2.

FIG. 3 is a chart explaining a method for determining a delay time in the delay time setting part 47 shown in FIG. 2.

In FIG. 3, the abscissa axis denotes cardiac time phase. As shown in FIG. 3, a R-R, a systole SD and a diastole DD of an ECG signal can be estimated from a HR with equation (1) and equation (2). Then, a delay time DTcor, for data acquisition, by which the influence of fluctuation in R-R is evaded can be set so as not to contradict the estimated R-R, systole SD and diastole DD.

For example, in the case of imaging under the FBI method, arteriovenous-separated blood flow image data can be generated with favorable contrast by acquisition of pieces of data in a systole and a diastole respectively every plural heart rates by a SSFP sequence or a FASE sequence and subtraction processing between the pieces of data corresponding to the diastole and the systole.

For that reason, a FASE sequence (FASEsys) for acquiring data in a systole SD and a FASE sequence (FASEdias) for acquiring data in a diastole DD are set for every plural heart rate. For that purpose, a delay time DTcor_sys from an R wave for the FASE sequence (FASEsys) for data acquisition of a systole SD and a delay time DTcor_dias from an R wave for the FASE sequence (FASEdias) for data acquisition of a diastole DD are set. That is each delay time DTcor_sys and DTcor_dias can be set at a timing changed temporally corresponding to a correction coefficient k for evading the influence of fluctuation in R-R, a delay time such as a TI of a fat saturation pulse and a TEeff so that pieces of data near the center of k-space are acquired respectively at desired timings in the systole SD and the diastole DD.

FIG. 3 shows an example where a delay time DTcor_sys for acquiring data in a systole SD and a delay time DTcor_dias for acquiring data in a diastole DD are set respectively by equation (6-1) and equation (6-2).

$$DTcor\_sys=SD/2+k-(TI+TEeff) \quad (6\text{-}1)$$

$$DTcor\_dias=SD+DD/2+k-(TI+TEeff) \quad (6\text{-}2)$$

Note that, a FASE sequence (FASEsys) for data acquisition in a systole SD and a FASE sequence (FASE dias) for data acquisition in a diastole DD may be performed in different heart rate periods mutually.

In the case of ECG-gated imaging under the TOF method, a delay time for data acquisition is set in either a diastole DD or a systole SD. In the case of ECG-gated imaging under the flow prep method, plural blood flow labeling pulses are applied as preparation pulses prior to an excitation pulse. Therefore, a delay time for data acquisition is changed by an echo time (TE) from an application timing of a labeling pulse to a data acquisition timing. In the case of the Flow Prep method, the data acquisition timing may be in either a systole SD or a diastole DD, or in both a systole SD and a diastole DD.

Next, a method of determining a correction coefficient k for evading the influence of fluctuation in R-R will be described.

Figure 4:
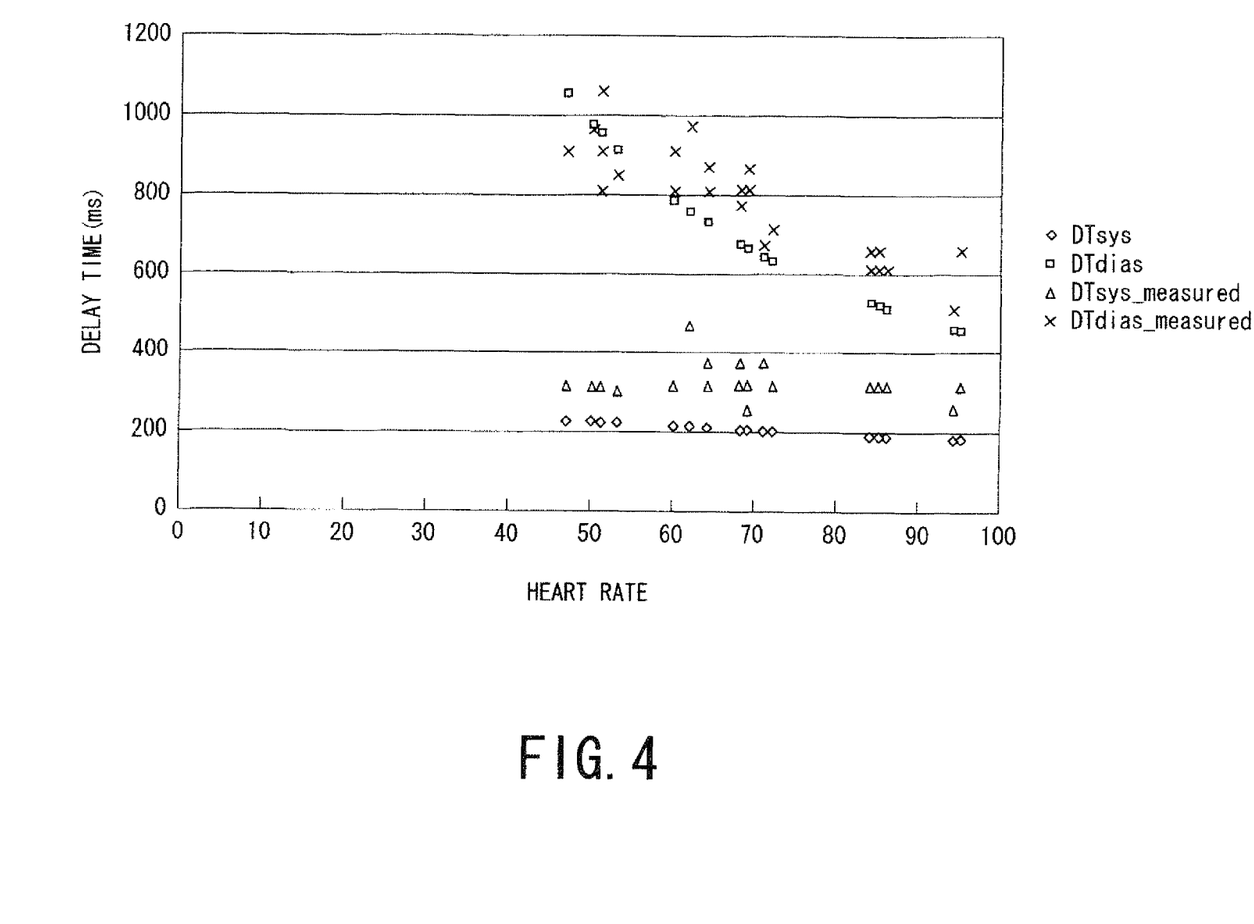
FIG. 4 is a graph for comparing delay times DT_measured used in the past with delay times DT before correction set in the delay time setting part shown in FIG. 2.
Figure 5:
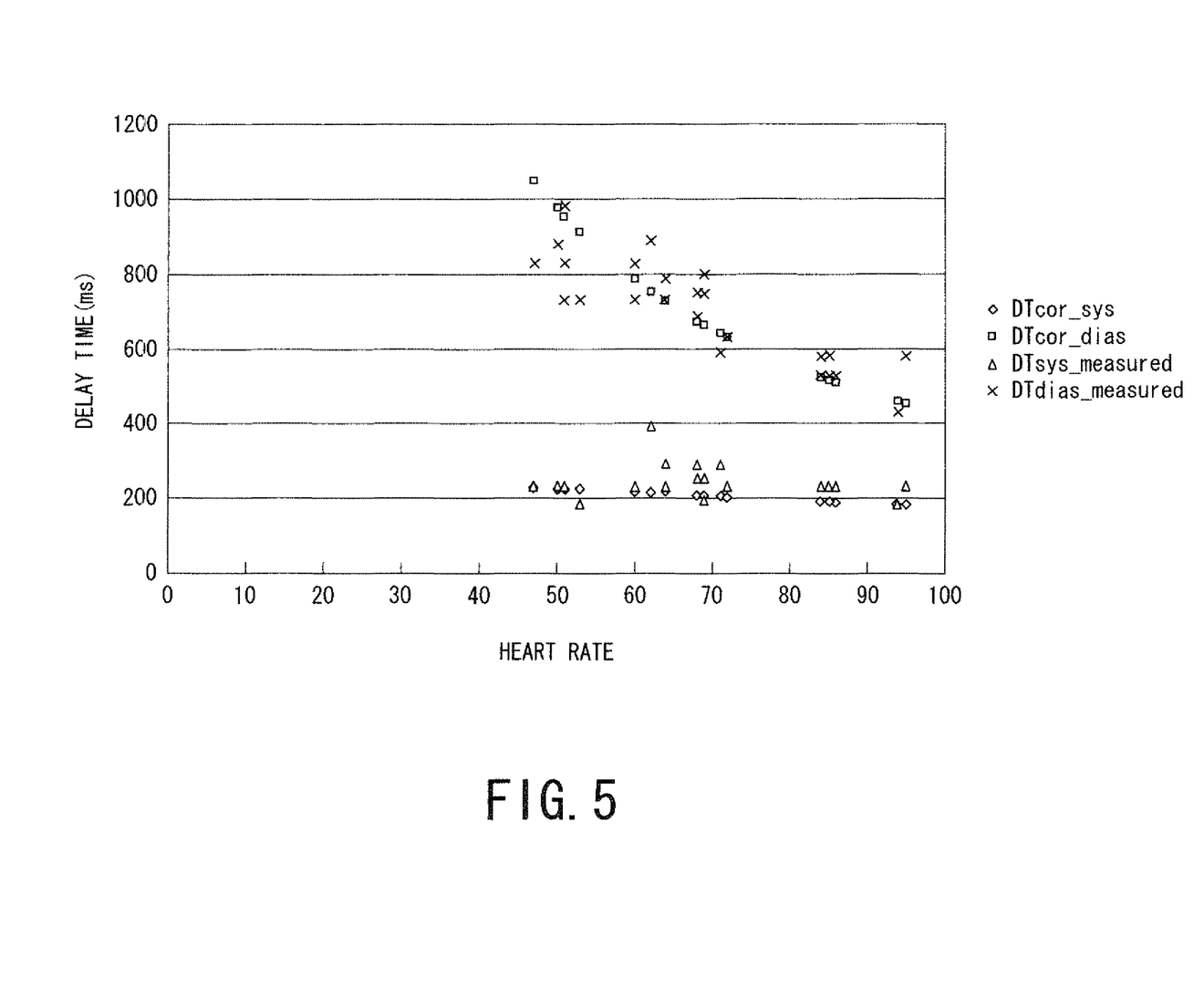
FIG. 5 is a graph showing an example of delay times DT_cor corrected according to the comparison graph shown in FIG. 4.

FIG. 4 is a graph for comparing delay times DT_measured used in the past with delay times DT before correction set in the delay time setting part 47 shown in FIG. 2. FIG. 5 is a graph showing an example of delay times DT_cor corrected according to the comparison graph shown in FIG. 4.

In FIGS. 4 and 5, each abscissa axis denotes HR and each ordinate axis denotes delay time (ms). When k in equation (6-1) and equation (6-2) is assumed to be 0 and delay times DTsys and DTsias before correction in a systole SD and a diastole DD are plotted every FIR, pieces of data shown by diamond marks and square marks of FIG. 4 are obtained. Meanwhile, when previous appropriate delay times DTsys_measured and DTdias_measured in a systole SD and a diastole DD determined in advance by an ECG-prep scan to acquire blood flow image data with changing a delay time from a reference wave such as an R wave on an FOG signal with regard to plural objects are plotted, pieces of data shown by triangular marks and cross marks of FIG. 4 are obtained.

Then, a value of correction coefficient k can be determined so that a deviation amount between the plot data of delay times DTsys in a systole SD before correction and the plot data of previous appropriate delay times DTsys_measured in a systole SD becomes small. In this case, fitting such as a least squares method can be used. Similarly, a value of correction coefficient k can be also determined so that a deviation amount between the plot data of delay times DTdias in a diastole DD and the plot data of previous appropriate delay times DTdias_measured in a diastole DD becomes small. Therefore, the correction coefficient k may be common between a systole SD and a diastole DD from the perspective of simplification of processing. Alternatively, the correction coefficient k may be set to different values between a systole SD and a diastole DD from the perspective of accuracy improvement.

When the delay times DTsys and DTdias in a systole SD and a diastole DD obtained by calculation is corrected using the correction coefficient k, corrected delay times DTcor_sys and DTcor_dias can be set to values closer to the previous appropriate delay times DTsys_measured and DTdias_measured respectively as shown in FIG. 5. Note that, in FIG. 5, the previous delay times DTsys_measured and DTdias_measured themselves are evaluated by parallel shift with using the correction coefficient k. The evaluation gives a result similar to that in a case where the delay times DTsys and DTdias obtained by calculation is corrected with using the correction coefficient k.

So far, a case of setting a delay time from a HR with using a calculation expression is described. As described above, a delay time can be also set based on a table relating HRs with delay times.

In the delay time table 48, delay times for respective ranges each corresponding to values of HR are stored as a table in advance. For example, the HR values are divided into three ranges like HR<50, 50<HR<70 and 70<HR, a appropriate delay time different according as each range of HR can be determined and stored in the delay time table 48. Moreover, similarly to a case of setting a delay time using a calculation expression, mutually different appropriate delay times can be related with respective ABI values, index values showing advancing extent of affected area and/or imaging parts and stored in the delay time table 48. The delay times stored in the delay time table 48 may be the delay times after correction with using a correction coefficient k.

When a delay time is set based on the table, the delay time setting part 47 is configured to obtain a corresponding delay time from the delay time table 48 based on information such as an ABI and/or an imaging part input from the input device 33.

Figure 6:
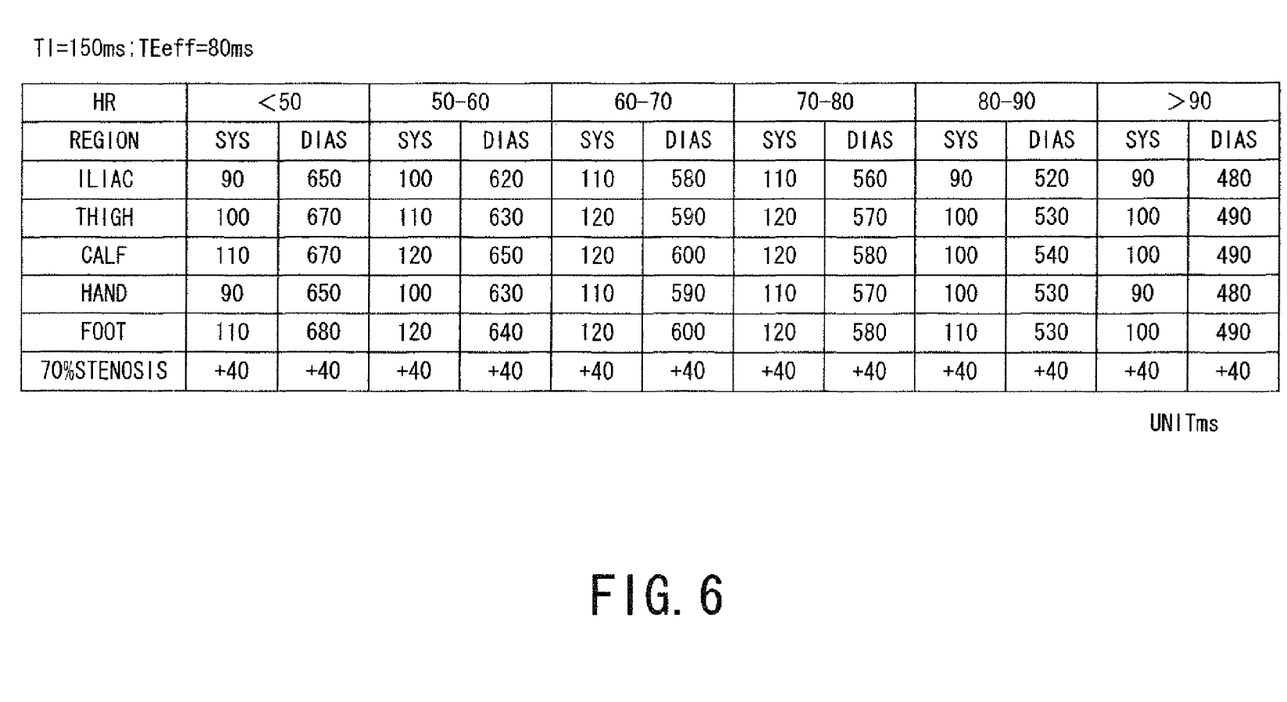
FIG. 6 shows an example of delay times stored in the delay time table shown in FIG. 2.

FIG. 6 shows an example of delay times stored in the delay time table 48 shown in FIG. 2.

As shown in FIG. 6, delay times according to HR values corresponding to a systole (SYS) and a diastole (DIAS) for respective imaging parts are stored in the delay time table 48. Note that, FIG. 6 shows an example case where TI=150 ms and TEeff=80 ms. In a case of 70% angiostenosis, the table is generated so that each delay time is set with addition by 40 ms.

Then, other functions of the computer 32 will be described.

The sequence controller control unit 41 has a function for controlling the driving of the sequence controller 31 by giving an imaging condition including a pulse sequence, received from the imaging condition setting unit 40, to the sequence controller 31, in response to instruction for scan start from the input device 33. Further, the sequence controller control unit 41 has a function for receiving raw data from the sequence controller 31 and arranging the raw data to k space formed in the k-space database 42. Therefore, the raw data generated by the receiver 30 is stored as k space data in the k-space database 42.

The image reconstruction unit 43 has a function for reconstructing image data from k-space data by capturing the k-space data from the k-space database 42 and performing image reconstruction processing including FT (Fourier transform) of the k-space data, and writing the generated image data to the image database 44. Therefore, the image database 44 stores the image data reconstructed by the image reconstruction unit 43.

The blood flow image generating unit 45 has a function for generating blood flow image data to be displayed by performing image processing such as subtraction processing and/or display processing such as MIP (maximum intensity projection) processing of necessary image data read from the image database 44 and a function for displaying a blood flow image on the display unit 34 by supplying the generated blood flow image data with the display unit 34. For example, blood flow data of arteries can be extracted by subtraction processing between image data generated based on k-space data acquired in a diastole and that in a systole for separation of veins and arteries.

(Operation and Action)

Then, the operation and action of the magnetic resonance imaging apparatus 20 will be described.

Figure 7:
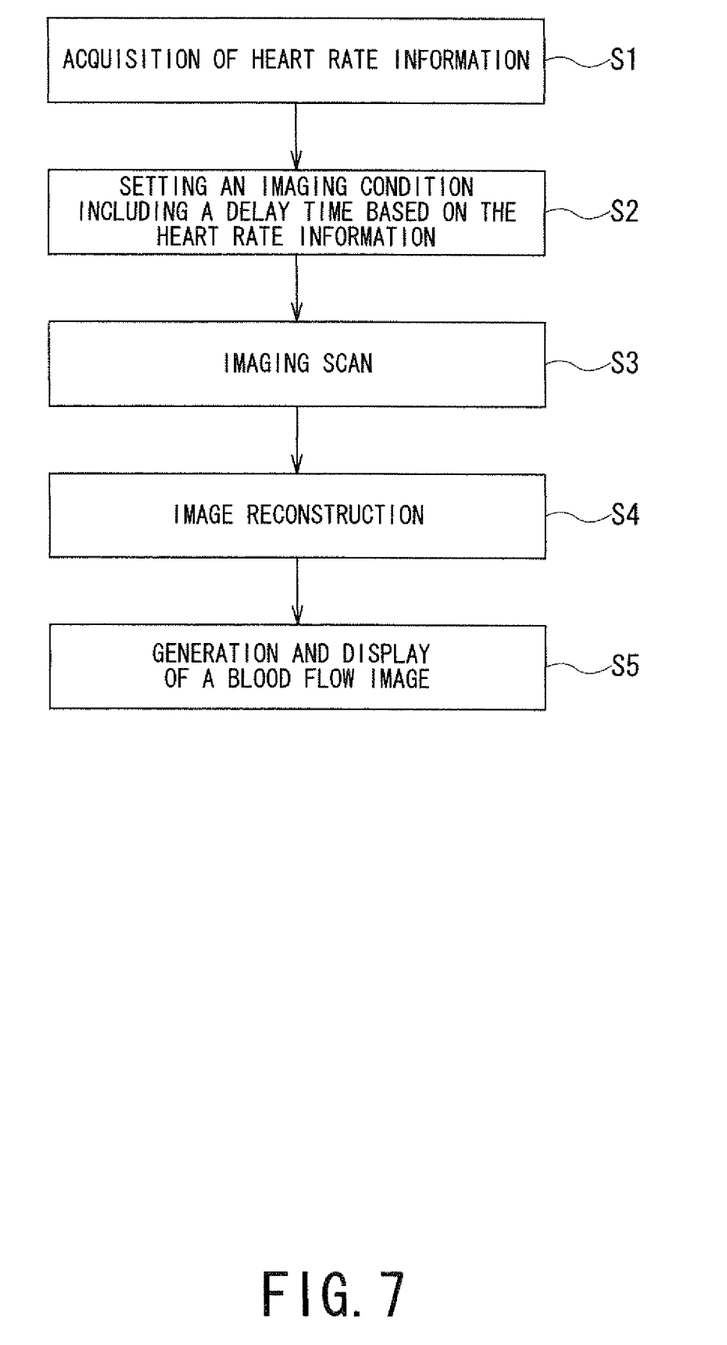
FIG. 7 is a flowchart showing a procedure for acquiring a blood flow image of an object by the magnetic resonance imaging apparatus shown in FIG. 1.

FIG. 7 is a flowchart showing a procedure for acquiring a blood flow image of an object P by the magnetic resonance imaging apparatus 20 shown in FIG. 1. The symbols each including S with a number in FIG. 7 indicate respective steps of the flowchart.

First, the object P is previously set to the bed 37, and a static magnetic field is generated at an imaging area of the magnet 21 (a superconducting magnet) for static magnetic field excited by the static-magnetic-field power supply 26. Further, the shim-coil power supply 28 supplies current to the shim coil 22, thereby uniformizing the static magnetic field generated at the imaging area.

Next, in step S1, a HR is acquired as heart rate information. Specifically, an ECG signal of an object P is acquired by the ECG unit 38. In the ECG unit 38, the HR is calculated by detecting an R wave from the acquired ECG signal. The acquired HR is output to the computer 32 from the ECG unit 38 through the sequence controller 31 with the ECG signal. Then, the HR is acquired by the heart rate acquisition part 46.

Next, in step S2, the imaging condition setting unit 40 sets a delay time based on the HR for a heart rate synchronization and an imaging condition for MRA including a pulse sequence. The delay time can be set based on the HR by the delay time setting part 47 referring to a relational expression representing a relation between HRs and delay times as described above or a table of delay times related to HR values stored in the delay time table 48. In addition, the delay time can be corrected depending on an ABI, an imaging part, an index value indicating an advance extent of an affected area, a delay time of a fat saturation pulse such as a TI and/or a TEeff. In addition, the delay time is corrected to an appropriate value with a correction coefficient k determined empirically in advance. Consequently, the pulse sequence as shown in FIG. 3 is set as the imaging condition.

Note that, the delay time setting part 47 may show a recommended value of delay time appropriate for an imaging condition such as an imaging part to a user through the display unit 34. In this case, the user can change the displayed recommended value of delay time by operation of the input device 33. Alternatively, plural alternatives in delay time corresponding to imaging conditions can be also displayed with selectability on the display unit 34.

Next, in step S3, an imaging scan with a delay time from an R wave is performed in synchronization with an ECG according to the set imaging condition to acquire data.

Specifically, the input device 33 sends instruction of scan start to the sequence controller control unit 41. The sequence controller control unit 41 supplies the imaging condition including a pulse sequence and a delay time for ECG synchronization received from the imaging condition setting unit 40 to the sequence controller 31. Therefore, the sequence controller 31 drives the gradient power supply 27, the transmitter 29, and the receiver 30 under ECG synchronization in accordance with the imaging condition received from the sequence controller control unit 41 and an ECG signal from the ECG unit 38, thereby generating a gradient magnetic field at an imaging area having the set object P, and further generating RF signals from the RF coil 24.

Consequently, the RE coil 24 receives NMR signals generated due to nuclear magnetic resonance in the object P. Then, the receiver 30 receives the NMR signals from the RE coil 24 and generates raw data by A/D conversion subsequently to necessary signal processing. The receiver 30 supplies the generated raw data to the sequence controller 31. The sequence controller 31 supplies the raw data to the sequence controller control unit 41. The sequence controller control unit 41 arranges the raw data as k-space data to the k space formed in the k-space database 42.

Then, the k-space data stored in the k-space database 42 is data acquired at timings determined by the delay time appropriate for generating blood flow image data, for example, in a myocardial systole and diastole.

Subsequently, in step S4, image reconstruction processing is performed by the image reconstruction unit 43. Specifically, the image reconstruction unit 43 reads the k-space data from the k-space database 42 and performs image reconstruction processing to the read k-space data, thereby generating image data. The generated image data is written in the image database 44.

Subsequently, in step S5, blood flow image data is generated by the blood flow image generating unit 45 and a blood flow image is displayed on the display unit 34. Specifically, the blood flow image generating unit 45 reads the image data from the image database 44 and performs necessary image processing of the image data, thereby generating blood flow image data for display. Subsequently, the generated blood flow image data for display is supplied to the display unit 34 and the blood flow image is displayed on the display unit 34. For example, artery image data is generated by subtraction processing between image data corresponding to a diastole and image data corresponding to a systole.

Therefore, a user can use the blood flow image, based on the data acquired at the appropriate timings, displayed on the display unit 34 for diagnosis.

That is, the magnetic resonance imaging apparatus 20 as mentioned above is an apparatus configured to automatically set a delay time from a reference wave to a data acquisition trigger necessary for a heart rate synchronous MRA or a peripheral pulse wave synchronous MRA based on heart rate information such as HR or peripheral pulse wave information.

(Effect)

Therefore, an appropriate time phase can be determined more easily and data can be acquired for a blood flow image without requiring a special knowledge and skill for a user according to the magnetic resonance imaging apparatus 20. Conventionally, though two dimensional multi time phase single scan like an ECG-prep scan was performed for determination of an appropriate delay time from a trigger such as an R wave, the delay time can be directly determined based on information of a patient, such as heart rate information or peripheral pulse wave information, acquired from an electrocardiograph or a sphygmograph to perform a three dimensional imaging scan without performing the pre-scan mentioned above.

In addition, according to the magnetic resonance imaging apparatus 20, for example, even in a case where an R-R interval fluctuates, a delay time can be corrected to an appropriate value so that influence of the fluctuation is reduced. Therefore, a delay time from a trigger signal to a data acquisition timing can be set automatically as an appropriate value more stably independent of characteristic of an object.

(Modifications)

1. First Modification

In the embodiment described above, an example where a delay time is determined depending on imaging conditions such as an R-R, a systole SD, a diastole DD and an imaging part and is corrected with using a correction coefficient k is described. However, as shown in FIG. 4, plotted data of previous appropriate delay times DTsys_measured and DTdias_measured regarding as plural objects per HR are acquired in advance by an arbitrary method such as an ECG-prep scan and the appropriate delay times for respective HRs may be stored in the delay time table 48. The empirical delay times for the respective HRs stored in the delay time table 48 may be a table that relates numerical values of delay time obtained by curve fitting of plotted data of the delay time to HR values or an approximate curve (function) that represents delay times for respective HRs obtained by curve fitting of the plotted data of the delay time.

Then, the delay time setting part 47 has only to acquire a HR of an object to become an imaging target from the heart rate acquisition part 46 to acquire an appropriate delay time corresponding to the HR by referring the delay time table 48 and automatically set the delay time as an imaging condition. In this case, the delay time stored in the delay time table 48 has a value corrected against an R-R fluctuation and is corrected by a period, such as a TI and/or a TEeff, to be changed. Therefore, it becomes possible to set a delay time by very simple processing.

For example, when a HR is read into the delay time setting part 47, the respective delay times corresponding to a diastole and a systole in a FBI sequence may be displayed on a setting screen of imaging condition with use of GUI (Graphical User Interface) as imaging parameters automatically and respective data acquisition triggers corresponding to the diastole and the systole can be generated automatically. Meanwhile, even if the respective delay times corresponding to the diastole and the systole are not displayed on the display unit 34, the respective delay times set automatically based on the HR can be held and used as imaging condition information in the imaging condition setting unit 40.

Note that, when delay times regarding different plural objects are obtained and an average delay time or delay times according to characteristics such as body types of objects are stored in the delay time table 48, it can be expected to reduce a setting error of delay time due to a difference in characteristic between the objects. In addition, as described above, when an appropriate delay time for every HR and every factors, such as a delay time DTF of a fat saturation pulse, a TEeff, an imaging part, an advancing extent of affected area and an ABI, which influences a delay time is stored in the delay time table 48, a more appropriate delay time can be set depending on a condition. Further, heart rate information such as an R-R or peripheral pulse wave information may be used instead of a HR.

2. Second Modification

When synchronization imaging is performed by using a PPG signal as described above, a sensor of a PPG signal detection unit is attached with an appropriate part of the object. In this case, a delay time from a reference wave of a PPG signal to a data acquisition trigger can be set automatically with a reference interval acquired from the PPG signal. Note that, while a HR is acquired from an ECG signal acquired separately, peripheral pulse wave synchronous imaging can be also performed by using a data acquisition trigger generated based on a PPG signal. In this case, it is necessary to convert a delay time for ECG synchronization determined based on a HR to a delay time for peripheral pulse wave synchronization.

For example, peripheral pulse wave synchronous imaging for a lower thigh can be performed by attaching a peripheral pulse wave sensor with a hand of an object together with acquiring a HR from an ECG signal. Here, a trigger obtained from the PPG signal shifts by a certain time to an R wave that is a reference wave of the ECG signal. Therefore, in the case of peripheral pulse wave synchronization, a delay time DTppg_cor from a trigger for the peripheral pulse wave synchronization can be obtained by adding a time difference $\Delta Decg\_ppg$ between an ECG signal and a PPG signal to a delay time DTecg_cor from an R wave for an ECG synchronizations obtained from a HR as shown in equation (7).

$$DTppg\_cor = DTecg\_cor + \Delta Tecg\_ppg \quad (7)$$

Therefore, when a peripheral pulse wave synchronous imaging is performed in a systole, a delay time DTppg_cor_sys in the systole for the peripheral pulse wave synchronization can be calculated by adding a time difference $\Delta decg\_ppg$ between a PPG signal and an ECG signal to a delay time DTecg_cor_sys in the systole for ECG synchronization obtained from a HR as shown in equation (8-1). Similarly, when a peripheral pulse wave synchronous imaging is performed in a diastole, a delay time DTppg_cor_dias in the diastole for the peripheral pulse wave synchronization can be calculated by adding a time difference $\Delta Decg\_ppg$ between a PPG signal and an ECG signal to a delay time DTecg_cor_dias in the diastole for ECG synchronization obtained from a HR as shown in equation (8-2). However, in the case of imaging in a diastole, a pulse wave delay time DTecg_cor_dias calculated by equation (8-2) may be longer than an R wave interval RR equivalent to a trigger interval of a PPG signal. In such a case, as shown in equation (8-3), the pulse wave delay time DTppg_cor_dias in the diastole can be calculated by subtracting the R wave interval RR from the sum of the ECG delay time DTecg_cor_dias in the diastole and the time difference $\Delta Decg\_ppg$.

$$DTppg\_cor\_sys = DTecg\_cor\_sys + \Delta Tecg\_ppg \quad (8\text{-}1)$$

$$DTppg\_cor\_dias = DTecg\_cor\_dias + \Delta Tecg\_ppg: \\ (DTecg\_cor\_dias + \Delta Tecg\_ppg) < RR \quad (8\text{-}2)$$

$$DTppg\_cor\_dias = (DTecg\_cor\_dias + \Delta Tecg\_ppg) - \\ RR : (DTecg\_cor\_dias + \Delta Tecg\_ppg) > RR \quad (8\text{-}3)$$

The time difference $\Delta Decg\_ppg$ between a PPG signal and an ECG signal is approximately 220 ms normally. Therefore, for example, when an R wave interval RR equivalent to a trigger interval of a PPG signal is 600 ms and an ECG delay time DTecg_cor_dias in a diastole obtained from a HR is 500 ms, the value derived by adding the time difference $\Delta Decg\_ppg = 220$ ms to the ECG delay time DTecg_cor_dias=500 ms of the diastole becomes 720 ms. Since this 720 ms is larger than the R wave interval RR=600 ms, a pulse wave delay time DTppg_cor_dias of the diastole is the value derived by subtracting the R wave interval RR=600 ms from 720 ms, i.e., 120 ms after the subsequent pulse wave trigger.

As mentioned above, also in the case of setting a delay time for peripheral pulse wave synchronous imaging based on heart rate information such as a HR, a table or a function relating heart rate information such as a HR with an appropriate peripheral pulse wave delay time may be stored in the delay time table 48 so as to be able to be referred and the stored relation information may be used for automatic setting, like the first modification.

3. Third Modification

In the embodiment described above, an example that a delay time is corrected by using a correction coefficient k for reducing the influence of fluctuation in reference wave interval such as R-R interval is described. However, the delay time may be used without the correction. In this case, when a systole SD is calculated, the systole SD may extend over the following heart rate. That is, there is a possibility that a data acquisition timing becomes just before an R wave. Therefore, it is preferable to calculate the systole SD within at least one heart rate thought to be the minimum.

For that reason, threshold processing function that sets a systole SD to the upper limit within a minimum heart rate period when the systole SD exceeds a threshold value corresponding to the minimum heart rate period can be provided with the delay time setting part 47. In other words, the equation (3) can be determined so that the delay time DT is calculated discontinuously depending on whether a HR exceeds a threshold value or not and the delay time DT is set to be short when the HR exceeds the threshold value.

What is claimed is:

1. A magnetic resonance imaging apparatus comprising:
   a heart rate acquisition unit configured to acquire a heart rate of a patient;
   a delay time setting unit configured to estimate a delay time from a reference wave in a blood flow beat of the patient, the estimated delay time corresponding to at least one of a systole and a diastole, and being estimated by using (i) the acquired heart rate and a calculation formula representing a relationship between delay times and heart rates or (ii) the acquired heart rate and a table showing a relationship between delay times and heart rates;

a data acquisition unit configured to acquire magnetic resonance signals from the patient with an imaging scan using the estimated delay time in synchronization with the blood flow beat of the patient; and an image generating unit configured to generate a blood flow image based on the acquired magnetic resonance signals.

2. A magnetic resonance imaging apparatus of claim 1, wherein said delay time setting unit is configured to estimate the delay time with correction for reducing an influence due to a fluctuation in an interval between blood flow beat reference waves.

3. A magnetic resonance imaging apparatus of claim 2, wherein said delay time setting unit is configured to add a correction coefficient to the delay time as the correction.

4. A magnetic resonance imaging apparatus of claim 3, wherein said delay time setting unit is configured to add a correction coefficient to the estimated delay time determined based on plural delay times, each of the plural delay times being related with previously acquired heart rate information or peripheral pulse wave information for the patient.

5. A magnetic resonance imaging apparatus of claim 1, wherein said delay time setting unit is configured to estimate the delay time based on a heart rate acquired by using an interval between adjacent R waves in an ECG signal.

6. A magnetic resonance imaging apparatus of claim 1, wherein said data acquisition unit is configured to perform an electrocardiogram synchronized imaging scan based on said blood flow beat.

7. A magnetic resonance imaging apparatus of claim 1, wherein said data acquisition unit is configured to repeatedly acquire the magnetic resonance signals during plural heartbeat R-R intervals.

8. A magnetic resonance imaging apparatus of claim 1, wherein said data acquisition unit is configured to acquire the magnetic resonance signals using a steady state free precession (SSFP) sequence.

9. A magnetic resonance imaging apparatus of claim 1, wherein said delay time setting unit is configured to estimate the delay time based on heart rate information by using a calculation formula representing a relationship between delay times and heart rate information.

10. A magnetic resonance imaging apparatus of claim 1, further comprising:

a storage unit configured to store delay times corresponding to respective values of heart rate information, wherein said data acquisition unit is configured to acquire a delay time corresponding to the heart rate information from the storage unit.

11. A magnetic resonance imaging apparatus of claim 1, wherein said delay time setting unit is configured to set a delay time also based on an imaged patient part and an ankle brachial index.

12. A magnetic resonance imaging apparatus of claim 1, wherein said delay time setting unit is configured to change the estimated delay time based on at least one of (a) a delay time from a fat saturation pulse to an excitation pulse and (b) an effective echo time.

13. A magnetic resonance imaging apparatus of claim 1, wherein said delay time setting unit is configured to set the estimated delay time using an acquired heart rate based on an average value of plural heart rates.

14. A magnetic resonance imaging apparatus of claim 1, wherein said delay time setting unit is configured to set the estimated delay time corresponding to the systole or the diastole to an upper limit within a minimum heart rate period in a case where the estimated systole or the diastole delay time exceeds a threshold value corresponding to a minimum heart rate period.

15. A magnetic resonance imaging apparatus of claim 1, wherein said delay time setting unit is configured to estimate a delay time also based on an index value indicating a degree of advanced condition for an affected area.

16. A magnetic resonance imaging apparatus of claim 1, wherein said data acquisition unit is configured to perform a scan in a diastole and a systole of a myocardium, respectively, and said image generating unit is configured to generate the blood flow image using subtraction processing between (a) acquired image data corresponding to the systole and (b) acquired image data corresponding to the diastole.

17. A magnetic resonance imaging apparatus of claim 1, wherein said data acquisition unit is configured to perform a three dimensional scan wherein the estimated delay time is based on the acquired heart rate derived from heart rate information or peripheral pulse wave information.

18. A magnetic resonance imaging apparatus of claim 1, wherein said delay time setting unit is configured to estimate a delay time for peripheral pulse wave gating imaging, the delay time being estimated based on the heart rate information.

19. A magnetic resonance imaging apparatus comprising:

a heart rate acquisition unit configured to acquire a heart rate of a patient;

a delay time setting unit configured to estimate a delay time from a reference wave in a blood flow beat of the patient, the delay time corresponding to at least one of a systole and a diastole, and being estimated by using the acquired heart rate and a table showing a relationship between delay times and heart rates, the relationship being acquired in advance of delay time estimation by an ECG-prep scan;

a data acquisition unit configured to acquire magnetic resonance signals from the patient with an imaging scan using the estimated delay time in synchronization with the blood flow beat of the patient, the delay time being acquired from said delay time setting unit; and an image generating unit configured to generate a blood flow image based on the acquired magnetic resonance signals.

20. A magnetic resonance imaging method comprising:

acquiring a heart rate of a patient;

estimating a delay time from a reference wave in a blood flow beat of the patient, the estimated delay time corresponding to at least one of a systole and a diastole, and being estimated by using the acquired heart rate and a calculation formula representing a relationship between delay times and heart rates, or by using the acquired heart rate and a table showing a relationship between delay times and heart rates;

acquiring magnetic resonance signals from the patient with an imaging scan using the estimated delay time in synchronization with the blood flow beat, the estimated delay time representing a time phase for image data acquisition synchronized with the blood flow beat, and generating a blood flow image based on the magnetic resonance signals.

21. A magnetic resonance imaging method comprising:
acquiring a heart rate of a patient;
estimating a delay time from a reference wave in a blood flow beat of the patient, the estimated delay time corresponding to at least one of a systole and a diastole, and being estimated by using the acquired heart rate and a table showing a relationship between delay times and heart rates, the relationship being acquired in advance of delay time estimation by an ECG-prep scan;
acquiring magnetic resonance signals with an imaging scan using the estimated delay time in synchronization with the blood flow beat; and
generating a blood flow image based on the magnetic resonance signals.

* * * * *